United States Patent [19]

Brunsting

[11] Patent Number: 4,657,398
[45] Date of Patent: Apr. 14, 1987

[54] SIMULTANEOUS MULTIPLE WAVELENGTH PHOTOMETER

[75] Inventor: Albert Brunsting, Elkhart, Ind.

[73] Assignee: Miles Laboratories, Inc., Elkhart, Ind.

[21] Appl. No.: 742,775

[22] Filed: Jun. 10, 1985

[51] Int. Cl.$^4$ ................................. G01J 3/51
[52] U.S. Cl. .................... 356/418; 350/315; 356/419
[58] Field of Search .............. 350/271, 315, 318; 356/414, 416, 418, 419, 320, 331, 332, 319

[56] References Cited

U.S. PATENT DOCUMENTS

| | | | |
|---|---|---|---|
| 3,416,864 | 12/1968 | Keahl et al. | 350/271 |
| 3,437,411 | 4/1969 | Rudomanski et al. | 356/418 |
| 3,834,817 | 9/1974 | Vinnemann et al. | 356/419 |
| 3,885,879 | 5/1975 | Louder et al. | 356/419 |
| 4,029,419 | 6/1977 | Schumann, Jr. et al. | 356/419 |
| 4,054,389 | 10/1977 | Owen | 356/332 |

OTHER PUBLICATIONS

Barnett et al., *Applied Optics*, vol. 16, No. 4, Apr. 1977, pp. 967-972.

*Primary Examiner*—F. L. Evans
*Attorney, Agent, or Firm*—Roger N. Coe

[57] ABSTRACT

Simultaneous multiple photometer measurements are made by simultaneously passing light to be measured through multiple light paths to different locations of a circularly variable filter; passing the light through the circularly variable filter at said locations; collecting the light passed through the circularly variable filter at each location; transmitting the light passed through the circularly variable filter to separate detectors; and measuring the light transmitted along each light path by said detectors.

3 Claims, 4 Drawing Figures

SIMULTANEOUS MULTIPLE WAVELENGTH PHOTOMETER

FIELD OF THE INVENTION

The present invention relates to a method and device for measuring reflected or transmitted light at multiple wavelengths and, more particularly, the present invention relates to a transmission type spectrophotometer or reflectance photometer capable of measuring transmitted or reflected light, respectively, simultaneously at multiple wavelengths by passing the transmitted or reflected light through a circularly variable filter at two or more positions and separately measuring the light passed through the filter at each location.

BACKGROUND OF THE INVENTION

The characteristics of light transmitted through or reflected by a specimen are related to the color of the specimen. With the advent of instrumental analysis, the color of a specimen under test has become one of the most widely used bases for biochemical assay procedures. For example, transmittance type spectrophotometric measurements are normally made by simply directing light through a cuvette containing a fluid sample to be analyzed. A portion of the light beam is absorbed by the sample and the remaining portions pass through the cuvette to photodetector means for measurement. By comparing the measurement obtained from the sample with a measurement obtained from a control fluid the concentration of the analyzed sample can be calculated.

Similarly, reagent test devices used for qualitative or quantitative analysis of body fluids are normally contacted for a prescribed period of time with a body fluid, such as blood or urine. The reflectance of the reacted test device will vary depending on the concentration of the analyte in the body fluid being examined. Thus, by photoelectrically measuring light reflected from the test device the desired analysis can be made by correlation of reflectance to reflectances obtained from known concentrations.

It is known that often times more information can be obtained about the analyte being measured if measurements are made at more than one wavelength. In addition, the accuracy of such measurements can be improved by taking measurements at more than one wavelength since such a procedure permits one to eliminate or reduce the influence of analyte interferences present at one wavelength and not another wavelength.

Spectrophotometers or reflectance photometers which have the capability of measuring light sequentially at different wavelengths are inherently subject to all of the errors which occur in making sequential measurements. Accordingly, a need has existed in the art for a method and device capable of making rapid, accurate, reproducible light measurements simultaneously at more than one wavelength.

The device and method of the present invention not only permit transmittance or reflectance measurements to be made simultaneously at more than one wavelength, but the method and apparatus permit the wavelengths at which measurements are made to be selected accurately, quickly and simply by rotating arms relative to the center of a circularly variable filter. Alternatively, the circularly variable filter can be rotated about its center.

SUMMARY OF THE INVENTION

An object of the present invention is to provide an improved photometer.

Another object of the present invention is to provide an accurate photometer capable of making transmittance or reflectance measurements simultaneously at at least two wavelengths.

Still another object of the present invention is to provide a spectrophotometer or a reflectance photometer capable of simultaneously making measurements at different wavelengths employing a circularly variable filter.

In accordance with the present invention, transmittance measurements are taken with a spectrophotometer or reflectance measurements are made by a reflectance photometer and then determined simultaneously at at least two different wavelengths. Such measurements, referred to herein as simultaneous, multiple photometer measurements, are made by simultaneously passing the light to be measured through multiple light passage paths to different locations of a circularly variable filter; passing the light through the circularly variable filter at said locations; collecting the light passed through the circularly variable filter at each location; transmitting the light passed through the circularly variable filter and collected at each location through separate light paths to separate detectors; and measuring the light transmitted along each light path by said detectors.

By passing transmitted or reflected light through a split fiber optic light path to and through a circularly variable filter (CVF) at two or more locations (determined by the position of means attached to the fiber optics which are rotatable relative to the CVF) the light transmitted through different portions of the CVF can be collected by suitable fiber optics and separately transmitted to measuring means. While any number of measurements can in principle be made, typically two to six different wavelengths are read simultaneously.

BRIEF DESCRIPTION OF THE DRAWINGS

Other and further objects, advantages, and features of the invention will be apparent to those skilled in the art from the following detailed description thereof, taken in conjunction with the accompanying drawings in which.

DESCRIPTION OF THE PREFERRED EMBODIMENTS

Figure 1:
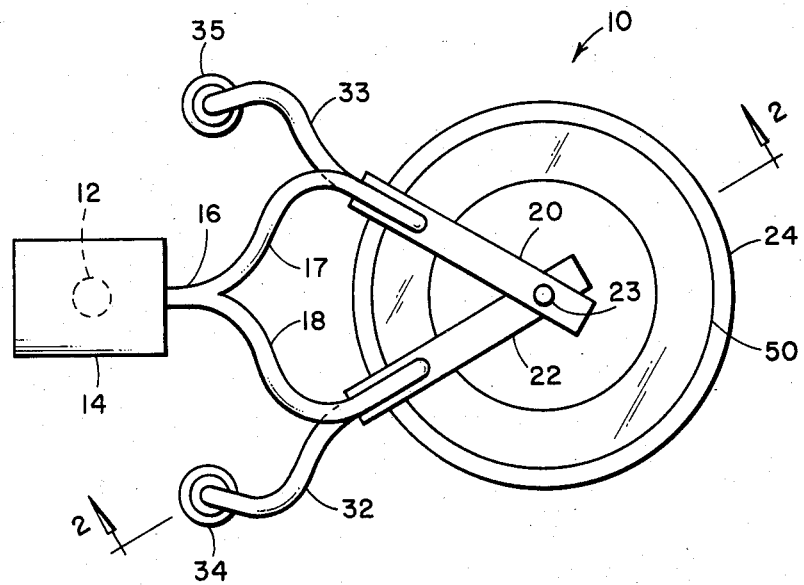
FIG. 1 is a diagrammatic top view illustrating photometer detection apparatus in accordance with the present invention.
Figure 2:
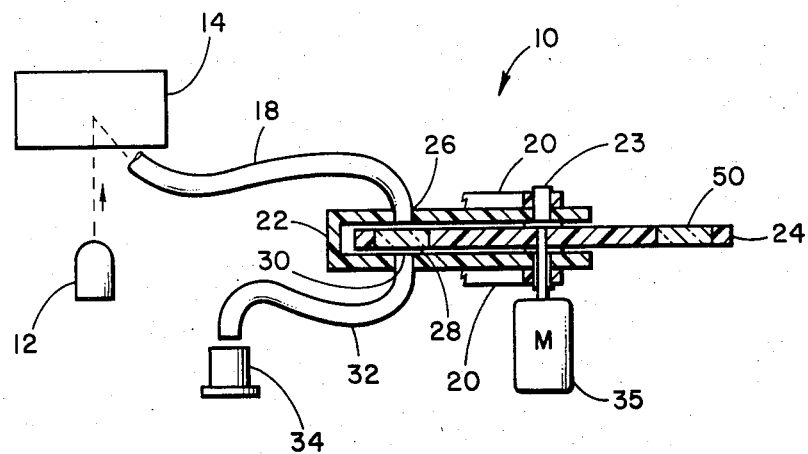
FIG. 2 is a diagrammatic side view, in partial cross-section, of the photometer of FIG. 1 taken along lines 1—1.

Referring now to the drawings, a simultaneous multiple wavelength photometer is illustrated in FIGS. 1 and 2. This photometer has a light source 12 which directs light onto a surface 14, e.g., a test strip or reagent test device. Light reflected from surface 14 passes through light transmission path 16 which is then split into two flexible light transmission paths 17 and 18. Light transmission paths 17 and 18 are connected at one end to light transmission path 16 and at their opposite ends light transmission paths 17 or 18 are respectively connected to rotatable means 20 and 22 which pivot around axis 23. Axis 23 is a common axis for a circularly variable filter 24.

The rotatable means 20 and 22 are U-shaped arm arrangements which interconnect to central axis 23 on the top and bottom sides of circularly variable filter 24. The U-shaped figuration of rotating arm 22, for example, permits this arm to be moved relative to circularly variable filter 24 thus positioning end 26 of light path 18 in alignment with a particular filter area 28 of circularly variable filter 24 such that when reflected light passing through light transmission path 18 is directed from end 26 through filter area 28 of circularly variable filter 24 the light entering end 30 of a light transmission path 32 has a particular wavelength which is different from the wavelength of the light passing through light transmission path 33. The light in light transmission paths 32 and 33 is measured using conventional photodetection means 34 and 35, respectively.

Figure 3:
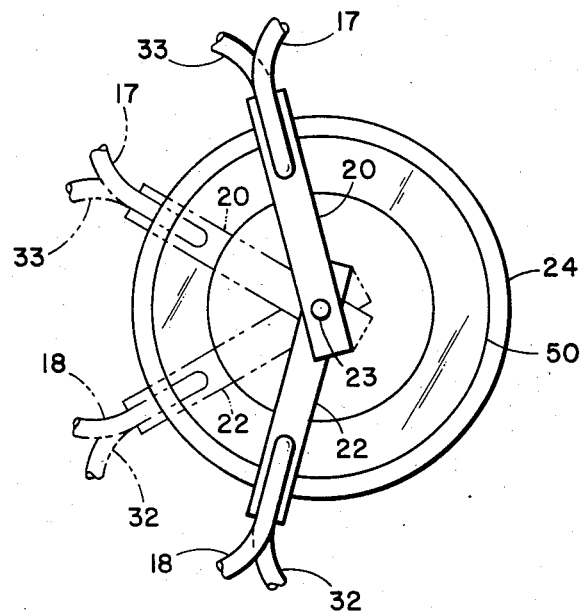
FIG. 3 is a partial diagrammatic top view of the photometer apparatus of FIG. 1 illustrating the adjustment of the means used to pass light through the circularly variable filter.

Thus, by varying the position of rotating means 20 and 22 as illustrated in FIG. 3 (the original positions being shown in phantom in FIG. 3), it is possible to make measurements at two entirely different wavelengths based on the new positions of rotating means 20 and 22 relative to circularly variable filter 24.

It will be understood that rotatable means or arms 20 and 22 can be rotated manually or automatically and that the circularly variable filter 24 can remain stationery or also be moved manually or automatically. One suitable means for moving rotatable means 20 and 22 and/or circularly variable filter 24 is motor 35 illustrated in FIG. 2. Other means, (not shown) could be employed to automatically program the location of the circularly variable filter and the rotatable arms.

While reflection measurements are specifically illustrated in FIGS. 1 and 2 it will be understood that transmission measurements can be measured precisely the same way by passing light from light source 12 through a transparent or translucent substance and then collecting the transmitted light in light transmission path 16.

The light transmission paths can be any suitable material. Preferably, fiber optics are employed which are sufficiently long and flexible to permit the adjustment of rotatable members 20 and 22 to any location relative to circularly variable filter 24.

While FIGS. 1 to 3 only illustrate the invention as having two rotatable means 20 and 22, to obtain simultaneous measurements at two different wavelengths, it will be understood that multiple arms can be present to facilitate making measurements at several different wavelengths. While in theory any number of wavelengths can be measured simultaneously by passing light through different locations of the circularly variable filter 24, in practice the number of wavelengths which are read simultaneously is normally between two and six.

Figure 4:
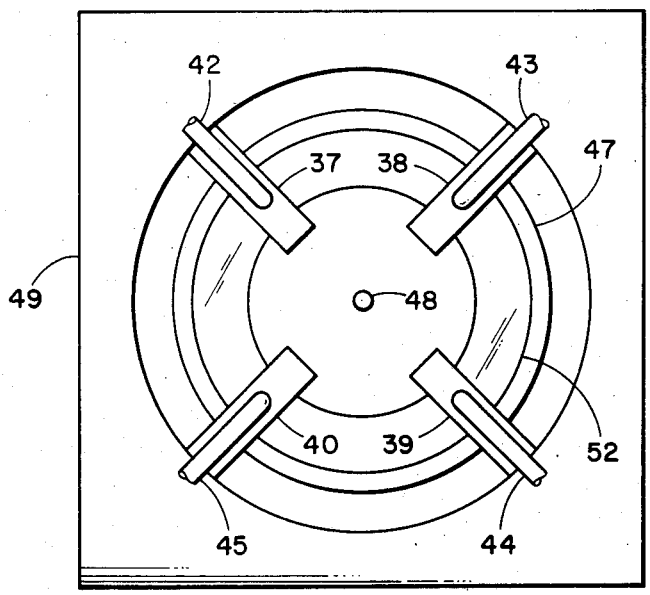
FIG. 4 is a diagrammatic top view illustrating another embodiment of photometric detection apparatus in accordance with the present invention.

In the embodiment illustrated in FIG. 4 rotatable means 37, 38, 39 and 40, which regulate the position of corresponding fiber optic members 42, 43, 44 and 45 relative to a circularly variable filter 47, are not connected to the axis 48 or any other portion of the circularly variable filter. Instead, such means are interconnected with a housing or member 49 which separately controls the movement of rotatable members 37–40 relative to circularly variable filter means 47.

Circularly variable filters 24 and 47 have the property that the center wavelength is proportional to the polar angle. A suitable circularly variable filter is available from Optical Coating Laboratories, Inc. of Santa Rosa, Calif. 95401 and sold under product number VC 180-017. The usable area of circularly variable filters 24 and 47 is shown as areas 50 and 52, respectively. While that circularly variable filters are illustrated as circles in the drawings it will be understood that, if desired, the shape of the filter can be semicircular (i.e., like VC 180-017 mentioned above) or wedge or pie shape if the wavelengths at which the readings are desired are somewhat more limited. Normally, the wavelengths at which measurements are taken will be at least 50 nanometers (nm) apart and the wavelengths will be chosen in the range of 400 to 700 nanometers.

Light source 12 can be any suitable light source, preferably a polychromatic light source, e.g., a tungsten lamp. Similarly, the detection means 34 and 35 can be selected from any suitable sensor, such as a solid state silicone photodiode, including UV 100 B made by E. G. and G Inc. of Salem, MA and Model S876-33BQ made by Hemamatsu Corp., Middlesex, N.Y.

From the foregoing, it will been seen that this invention is well adapted to attain all of the ends and objects hereinbefore set forth, together with other advantages which are obvious and inherent. Both end and kinetic tests can be accomplished with the method and apparatus of the present invention. The invention provides for simultaneously measuring light at multiple wavelengths with an instrument having substantial flexibility. The wavelengths at which measurements are taken can be changed at will, limited only by the range of wavelengths available using a particular circularly variable filter.

Obviously, many modifications and variations of the invention as hereinbefore set forth can be made without departing from the spirit and scope thereof and therefore only such limitations should be imposed as are indicated by the appended claims.

What is claimed is:

1. Apparatus for simultaneously measuring light at multiple wavelengths which are at least 50 nanometers apart and within the range of 400 to 700 nanometers comprising:
    a circularly variable filter;
    means for passing the light along multiple light transmission paths to the circularly variable filter;
    means for passing said light through the circularly variable filter at at least two separate positions of the circularly variable filter which are at wavelengths 50 nanometers apart and within the range of 400 to 700 nanometers;
    separate detection means for measuring each wavelength of the light passed through the circularly variable filter; and
    means for simultaneously moving the means for passing light through the circularly variable filter and the detection means relative to said circularly variable filter.

2. The apparatus of claim 1 wherein the means for simultaneously moving the means for passing light through the circularly variable filter and the detection means relative to said circularly variable filter is a U-shaped arm interconnected to the central axis of the circularly variable filter.

3. Apparatus for simultaneously measuring light at multiple wavelengths which are at least 50 nanometers apart and within the range of 400 to 700 nanometers comprising a housing containing:
- a circularly variable filter;
- means for passing the light along multiple light transmission paths to the circularly variable filter;
- means for passing said light through the circularly variable filter at at least two separate positions of the circularly variable filter at wavelengths at least 50 nanometers apart and within the range of 400 to 700 nanometers;
- separate detection means for measuring each wavelength of light passed through the circularly variable filter; and
- means attached to the housing for simultaneously moving the means for passing light through the circularly variable filter and the detection means relative to said circularly variable filter.

* * * * *